(12) United States Patent
Hale (10) Patent No.: US 8,529,444 B2
(45) Date of Patent: Sep. 10, 2013

(54) FLEXIBLE SURGICAL RETRACTOR

(76) Inventor: Theodore Hale, Bronx, NY (US)

(*) Notice: Subject to any disclaimer, the term of this patent is extended or adjusted under 35 U.S.C. 154(b) by 1272 days.

(21) Appl. No.: 12/020,014

(22) Filed: Jan. 25, 2008

(65) Prior Publication Data

US 2009/0192359 A1    Jul. 30, 2009

(51) Int. Cl.
| | |
|---|---|
| A61B 1/32 | (2006.01) |
| A61B 17/08 | (2006.01) |
| B25B 1/00 | (2006.01) |
| B25B 1/24 | (2006.01) |
| F16M 1/00 | (2006.01) |
| F16M 3/00 | (2006.01) |
| F16M 5/00 | (2006.01) |
| F16M 7/00 | (2006.01) |
| F16M 9/00 | (2006.01) |
| F16M 11/00 | (2006.01) |
| F16M 13/00 | (2006.01) |

(52) U.S. Cl.
USPC ........... 600/206; 606/158; 269/275; 267/136; 248/615

(58) Field of Classification Search
USPC .................. 600/206, 207, 208, 210; 81/458, 81/486, 22; 269/275; 294/33; 267/133, 267/136, 137, 139, 140.11, 141; 248/615; 606/99, 157, 158; 128/885
See application file for complete search history.

(56) References Cited

U.S. PATENT DOCUMENTS

| | | | |
|---|---|---|---|
| 3,147,754 A * | 9/1964 | Koessler ........................ | 128/885 |
| 3,231,256 A * | 1/1966 | Olson ............................ | 267/153 |
| 3,269,717 A * | 8/1966 | Beck ............................. | 267/141 |
| 3,462,330 A * | 8/1969 | Greig et al. ................... | 156/210 |
| 3,503,398 A * | 3/1970 | Raible et al. .................. | 606/207 |
| 3,675,656 A * | 7/1972 | Hakim .......................... | 606/158 |
| 3,866,611 A * | 2/1975 | Baumrucker ................. | 128/885 |
| 3,993,076 A * | 11/1976 | Fogarty ........................ | 606/158 |
| 4,106,508 A * | 8/1978 | Berlin .......................... | 606/158 |
| 4,562,832 A | 1/1986 | Wilder et al. | |
| 4,777,943 A | 10/1988 | Chvapil | |
| 4,781,365 A * | 11/1988 | Harrison ...................... | 267/294 |
| 4,846,518 A * | 7/1989 | Hamel ......................... | 294/99.1 |
| 5,072,720 A * | 12/1991 | Francis et al. ................ | 600/186 |
| 5,080,088 A * | 1/1992 | LeVahn ........................ | 600/206 |
| 5,308,327 A * | 5/1994 | Heaven et al. ............ | 604/103.09 |
| 5,522,791 A | 6/1996 | Leyva | |
| 5,624,454 A * | 4/1997 | Palti et al. .................... | 606/151 |
| 5,674,243 A | 10/1997 | Hale | |
| 5,881,981 A * | 3/1999 | Yanagisawa ............... | 248/188.8 |

(Continued)

FOREIGN PATENT DOCUMENTS

EP      1487349      12/2004

OTHER PUBLICATIONS

Li-Jen Kuo, et al. Femoral Neuropathy After Surgery, Journal of The Chinese Medical Association, vol. 67, No. 12, pp. 644-646.

(Continued)

*Primary Examiner* — David Bates (74) *Attorney, Agent, or Firm* — Tutunjian & Bitetto, P.C.

(57) ABSTRACT

A surgical retractor including a slab-shaped member having a first edge and a second opposing edge, wherein a deformable elongate member is provided affixed to said first edge, said elongate member comprising an external wall defining an internal chamber, wherein the external wall is configured to be compressible and moldable to a surface, in particular, a human tissue surface within a surgical incision. A curved flexural handle may be provided attached to the second edge.

14 Claims, 6 Drawing Sheets

(56) References Cited

U.S. PATENT DOCUMENTS

| | | | |
|---|---|---|---|
| 6,139,493 A | 10/2000 | Koros et al. | |
| 6,241,658 B1 | 6/2001 | Goodrich | |
| 6,284,346 B1* | 9/2001 | Sheridan | 428/156 |
| 6,537,212 B2 | 3/2003 | Sherts et al. | |
| 6,582,364 B2 | 6/2003 | Butler et al. | |
| 6,692,514 B2* | 2/2004 | Fogarty et al. | 606/207 |
| 6,796,940 B2* | 9/2004 | Bonadio et al. | 600/206 |
| 6,805,662 B2* | 10/2004 | Shah et al. | 600/29 |
| 6,814,700 B1 | 11/2004 | Mueller et al. | |
| 7,033,319 B2 | 4/2006 | Pulford et al. | |
| 7,331,534 B2* | 2/2008 | McQueen | 238/283 |
| 8,011,356 B2* | 9/2011 | Gordon et al. | 124/88 |
| 2003/0060685 A1* | 3/2003 | Houser et al. | 600/206 |
| 2004/0005438 A1* | 1/2004 | Lichodziejewski et al. | 428/166 |
| 2006/0112477 A1* | 6/2006 | Schneider | 2/412 |
| 2007/0066872 A1* | 3/2007 | Morrison et al. | 600/212 |

OTHER PUBLICATIONS

John A. Rock, Howard W. Jones III. Telinde's Operative Gynecology. Ninth Edition. pp. 246, 248-249.

* cited by examiner

FLEXIBLE SURGICAL RETRACTOR

BACKGROUND OF THE INVENTION

1. Technical Field of the Invention

The present invention generally relates to surgical retractors, and, more particularly, to an abdominal retractor assembly configured for maintaining access to a cavity within the human abdomen after insertion therein during intra-abdominal surgery while minimizing trauma to the surrounding soft tissue, nerves and vessels.

2. Description of Related Art

In the medical field, retractors are used to hold tissue away from the operative area to improve exposure during surgical procedures. Surgical retractors, namely abdominal retractors, are typically inserted within abdominal incisions during surgery to forcibly enlarge the area of incision and facilitate access within the abdomen. Rigid metal retractors comprising implements formed of, e.g., stainless steel, are well-known, having the advantage of being durable as well as being easy to sterilize and sanitize for repeated surgical use.

Retractors may be held by an assistant (manual retractors) or utilize counter-pressure from other tissue (self-retaining retractors) to maintain proper placement. Numerous self-retaining as well as manual retractors, typically made of metal, are known, some examples being the O'Conner-O'Sullivan retractor, and the Balfour, Bookwalter, Heaney, Deaver and Richardson retractors. During a typical use, metal retractors are placed at opposing edges of a linear incision and are caused to move away from each other to effectuate incision expansion.

Rigid metal retractors however, can be a cause for concern when used in certain surgical procedures, in particular, those requiring surgical incision within the abdominal/pelvic area, due to the risk of further trauma, compression or injury to the surrounding delicate soft tissue with its abundant network of vessels and nerves.

While retractors composed of non-metal materials are disclosed, e.g., in U.S. Pat. No. 4,562,832, such retractors are typically constructed to be rigid and resistant to deformation. Alternate types of retractors include an adjustable retractor such as shown in U.S. Pat. No. 7,033,319 composed of an inner and outer ring connected by an elongate sleeve, which is configured for expanding incisions in a circular shape. Further, a deformable retractor is shown in U.S. Pat. No. 5,522,791 which is structured for retracting a linear incision and forming the surrounding tissue into a generally circular configuration.

However, retractors having a rigid, non-deformable construction and/or which forcibly expand a surgical incision into a predetermined shape may be undesirable for certain surgical procedures and present the risk of undue injury or trauma to the delicate soft tissue underlying the area of the incision. In particular, some conventional retractors appear to contribute to postoperative femoral neuropathy, namely femoral nerve injury, in patients undergoing abdominal/pelvic surgery, due to direct compression of the femoral nerve during use and placement.

One of the main post-operative complications caused by intra-abdominal surgery is bowel ileus, which causes severe injury to the patient and long hospital stays. In addition, pulmonary embolism is a serious concern which causes a high number of deaths because of small and large blood clots due to vascular stasis, bowel packs left within the incision, or from rigid retractors.

Accordingly, a need exists for a surgical retractor for effectively expanding an incision site while minimizing trauma to the surrounding tissues, nerves and vessels and potential morbidity resulting therefrom.

SUMMARY OF THE INVENTION

In view of the foregoing, the primary object of the present invention is to provide an improved surgical retractor, namely for use with abdominal incisions, which is effective in maintaining the retraction of the tissues of surgical site while preventing damage thereat.

As such, the present invention generally relates to surgical retractors, and, more particularly, to an abdominal retractor assembly configured for effectively expanding an abdominal incision while minimizing in-situ physiological traumatic effects, namely avoiding injury, compression and damage to the soft tissue, blood vessels, nerves, etc. in the vicinity of the incision site.

Advantageously, an abdominal retractor according to an aspect of the present invention is configured to self-mold within the abdominal surgical cavity, e.g., in particular, the retroperitoneum, providing effective yet safe retraction of the abdominal tissue during surgical procedures. It is noted that the retroperitoneal space of the human abdomen is in the form of a delicate U-shape with a rich network of nerves, ureters and hypogastric blood vessels.

A surgical retractor according to one embodiment of the present invention preferably comprises e.g., a slab or blade-shaped unit having at least a flexible elongate member disposed at a first end, and a handle attached to an opposing end thereof. The flexible elongate member may comprise a plurality of sides defining an elongate cavity. For example, the elongate member may have six sides so as to be hexagonal in cross-section.

The cavity may be a hollow open air chamber or may include an internal lattice structure, e.g., a series of flexible air-filled cells having a multi-sided configuration. For example, the internal lattice network may comprise a 'honeycomb' network wherein a longitudinal axis of the air chambers is substantially parallel to a longitudinal axis of the elongate member.

In addition, the walls of the elongate member may further be comprised of a flexible, moldable material (e.g., polyurethane) having an internal lattice structure, for example, air-filled cells in a 'honeycomb' configuration. In both the cell network of the cavity and/or the cell network of the walls, preferably, an open-cell configuration is employed. Accordingly, the elongate member is freely compressible and moldable to the shape of any surface it is contacted with.

A surgical retractor according to another embodiment may comprise a deformable polyurethane elongate member having an external wall defining an internal chamber, wherein the internal chamber includes a cross-linked polyurethane cell lattice structure and the external wall is configured to be compressible and moldable to a surface. The deformable elongate member may be configured to be affixed to the frames of existing surgical retractors, e.g., be attached onto a desired/suitable edge of any other existing retractor frame for use therewith.

Advantageously, according to one aspect, the flexible elongate member having internal open air chambers in combination with the honeycomb-shaped, hydrophilic polyurethane walls impart desirable cushioning properties to the blade-shaped unit. This, in turn, substantially reduces or eliminates damage to surrounding nerve tissue in contact with the retractor during use (e.g., when a force is applied to the elongate member). The polyurethane may include hydrophilic properties and accordingly becomes softer when contacted with wet or moist surfaces.

Namely, the elongate member maximizes the surface area over which the applied force is distributed, e.g., by custom molding to the shape of the surface with which it is contacted. By distributing the force over a greater surface area, pressure points are reduced or eliminated when the force is applied or exerted on the blade-shaped unit. Accordingly, damage or injury to the underlying delicate tissues in the incision site subject to the force is prevented.

According to one aspect of the present invention, a surgical retractor is provided comprising a slab-shaped member having a first edge and a second opposing edge, and a deformable elongate member affixed to said first edge, said elongate member comprising an external wall defining an internal chamber, wherein the external wall is configured to be compressible and moldable to a surface.

According to another aspect, a self-molding surgical retractor is provided comprising a slab-shaped member having a first edge and a second opposing edge, a deformable elongate member affixed to said first edge, said elongate member comprising an external wall defining an internal chamber, wherein the external wall comprises a plurality of sides and is configured to be compressible and moldable to a surface. A curved handle is provided attached to the second edge.

According to yet another aspect, a surgical retractor is provided comprising a deformable polyurethane elongate member comprising an external wall defining an internal chamber, wherein the internal chamber includes a cross-linked polyurethane cell lattice structure and the external wall is configured to be compressible and moldable to a surface.

These and other aspects, features, and advantages of the present invention will be described or become apparent from the following detailed description of the preferred embodiments, which is to be read in connection with the accompanying drawings.

BRIEF DESCRIPTION OF THE DRAWINGS

In the drawings, wherein like reference numerals denote similar elements throughout the views.

It should be understood that the drawings are for purposes of illustrating the concepts of the invention and are not necessarily the only possible configurations for illustrating the invention.

DETAILED DESCRIPTION OF PREFERRED EMBODIMENTS

A surgical retractor assembly in accordance with an aspect of the present invention, advantageously provides a unique self-molding design providing improved functionality and safety. Namely, a flexible surgical retractor is provided for effective retraction of a surgical incision while self-molding to the shape and contours of soft tissue underlying the incision. In particular, the retractor is specially adapted to conform to the contours of tissue within the abdominal cavity, such as the retroperitoneal space.

A resultant retractor assembly according to an aspect of the present invention provides effective tissue retraction while preventing surgical interference and injury or damage to the site.

Figure 1:
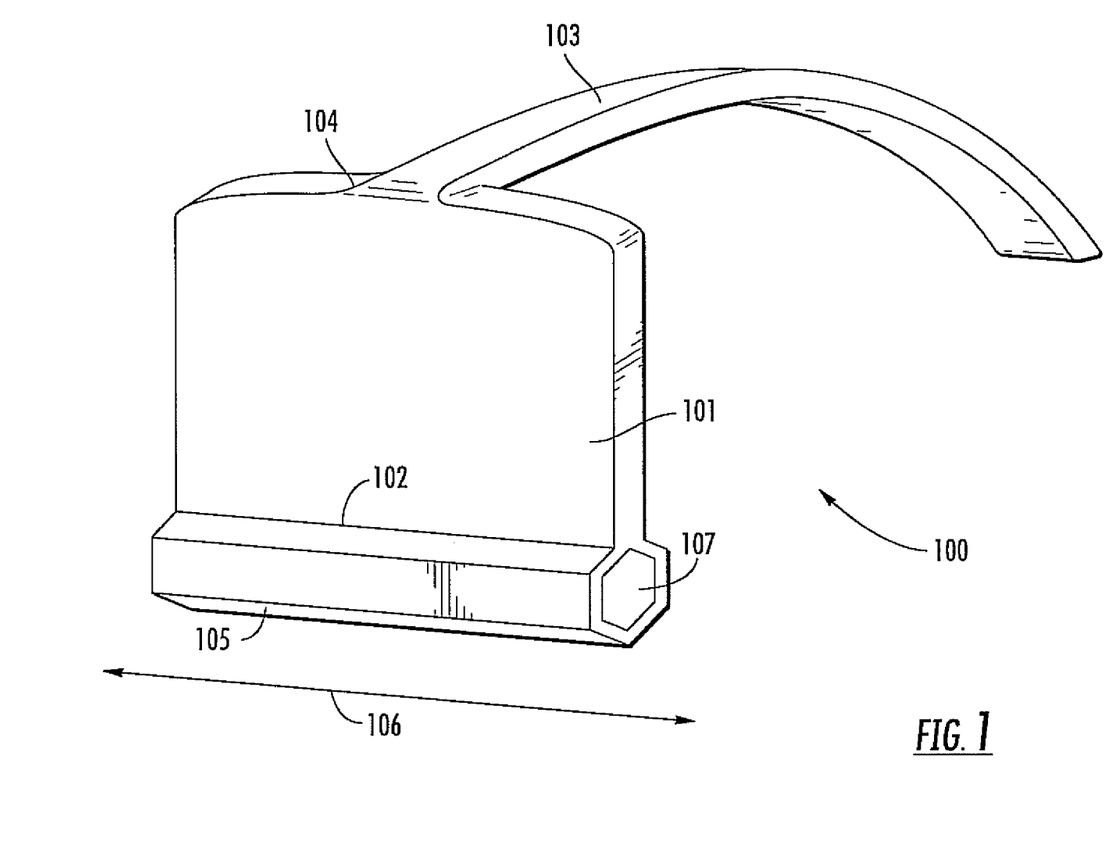
FIG. 1 is an exemplary front perspective view of a retractor assembly according to an aspect of the present invention.
Figure 2A:
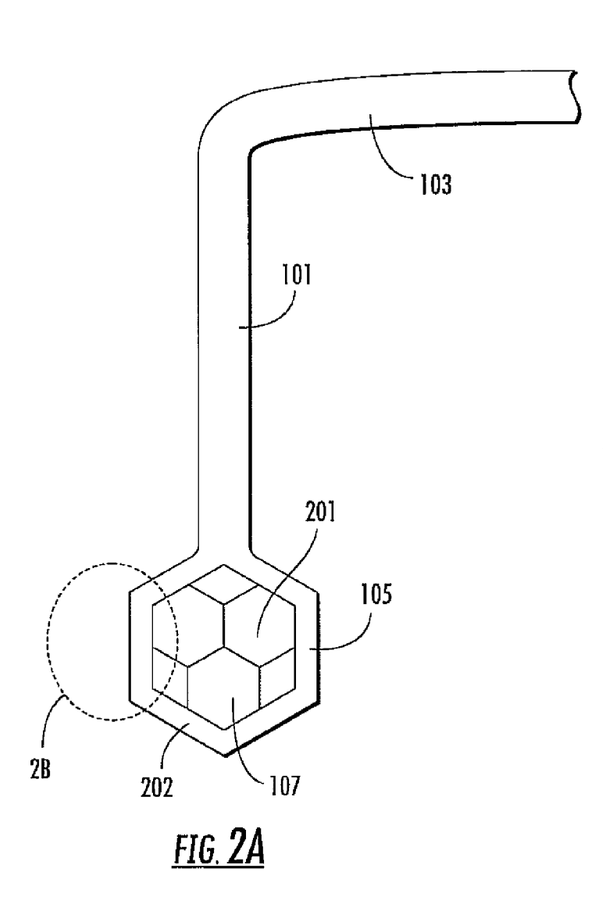
FIG. 2A is an exemplary partial side view of a retractor assembly according to an aspect of the present invention.
Figure 2B:
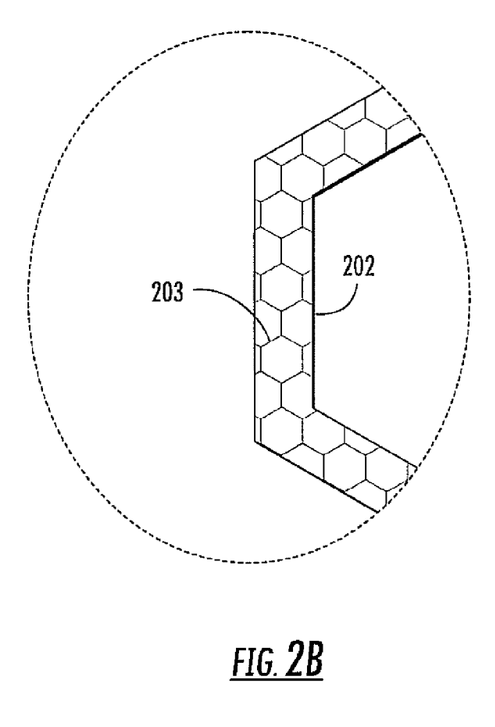
FIG. 2B is an exemplary enlarged view of area "A" of FIG. 2A according to an aspect of the present invention.

An exemplary surgical retractor assembly 100 and various exemplary views thereof are illustrated in FIGS. 1, 2A and 2B. The retractor 100 comprises a slab or blade-shaped member 101 having a first edge 104 and a second opposing edge 102. In one example, the slab-shaped unit 101 may measure approximately 2.5 inches in width and 3.5 inches from top to bottom. Exemplary materials from which the slab-shaped member 101 may be comprised may include graphite, graphite composite, carbon fiber, polyurethane, etc., and any combination of the above.

An elongate handle 103 may be provided affixed to the first edge 104, and is preferably comprised of a rigid material in any shape, e.g., tubular, polygonal, and may further include ergonomic features to assist in gripping and comfort during handling. While the handle 103 may be comprised of any desired shape and length, in a preferred embodiment the handle is curved or arched such that a longitudinal axis of the handle 103 comprises an arcuate form, preferably curving downwards.

Advantageously, a downwards curving handle shape assists in keeping the retractor 100 out of the operating field, thus preventing the retractor 100 from encroaching on the surgeon's standing area and/or interfering with the surgeon's movements during surgery.

The handle 103 is preferably comprised of a semi-rigid material, which is strong, durable, crack-resistant and maintains its curved configuration yet provides a degree of flexion when subject to force or pressure, advantageously providing a measure of shock absorption during use. Exemplary materials may include, e.g., polyurethane, silicone, polyethylene, carbon fiber compounds, rubber, spring steel, etc., and composites thereof. In one example, a preferred handle material comprises carbon fiber and/or graphite composite added to polyurethane.

A deformable elongate member 105 may be provided affixed to the second edge 102 of the blade-shaped unit 101. The member 105 may comprise, e.g., an elongate structure having an external wall 202 defining an internal cavity 107. In one embodiment, the wall 202 may be comprised of a plurality of flat sides so as to be substantially polygonal in side view and/or cross-section.

For example, as shown in the example depicted in FIGS. 1 and 2A, the member 105 may comprise a six-sided wall so as to be substantially hexagonal in side view/cross-section; that is, comprise a 'honeycomb' shape. An alternate embodiment may be contemplated wherein the elongate member 105 is formed into a teardrop shape (when viewed in cross-section or from the side). Other polygonal shapes, e.g., triangular, rectangular, octagonal, etc., as well as circular, oval or elliptical shapes may be contemplated.

The elongate member 105 is the component which makes direct contact with the human tissue when inserted into an incision site, and is preferably comprised of a thin, flexible, ultra-soft medical-grade material. For example, the walls 202 of the elongate member 105 may be comprised of polyurethane or a polyurethane-based material and adapted to advantageously self-mold to the shape of the tissue with which it is being contacted. Further, the polyurethane used may preferably include hydrophilic properties which advantageously causes it to become softer when contacted with wet or moist surfaces.

Figure 3:
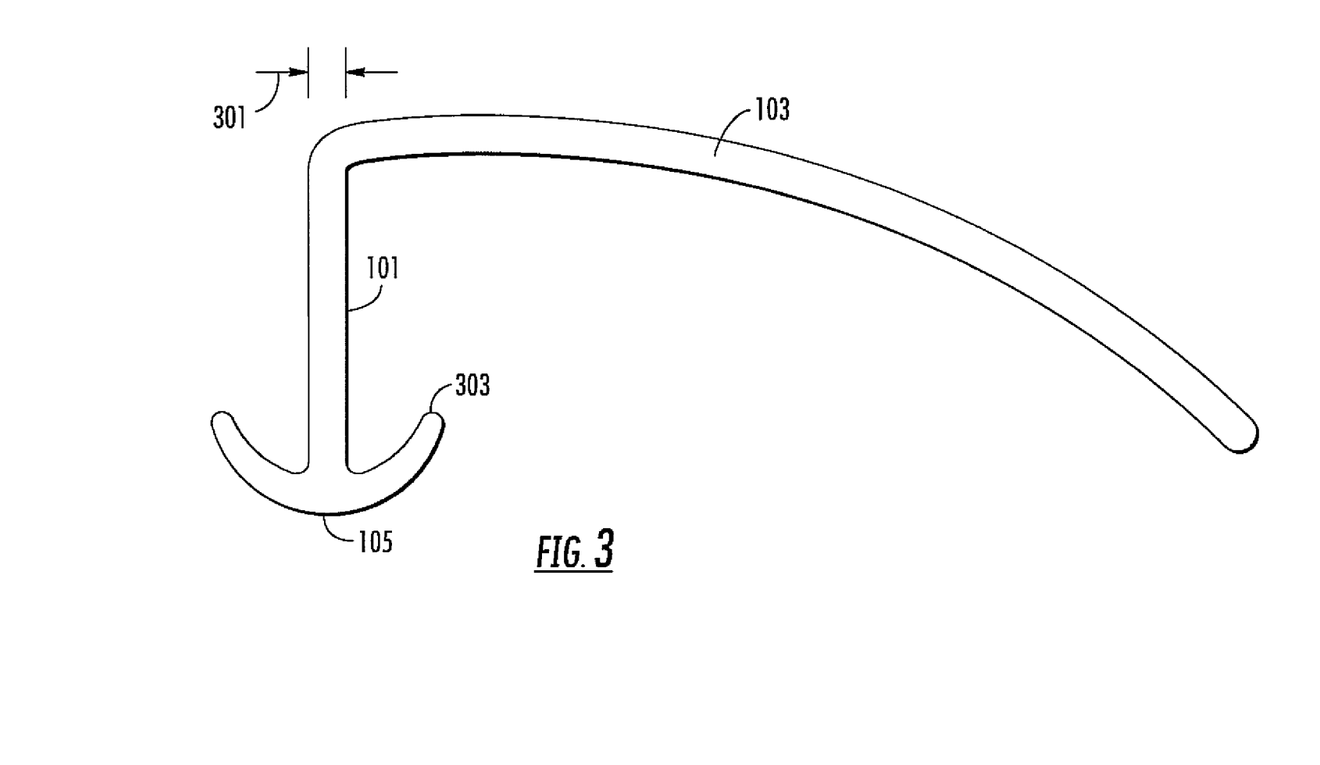
FIG. 3 is an exemplary side view of a retractor in a compressed position according to an aspect of the present invention.
Figure 4:
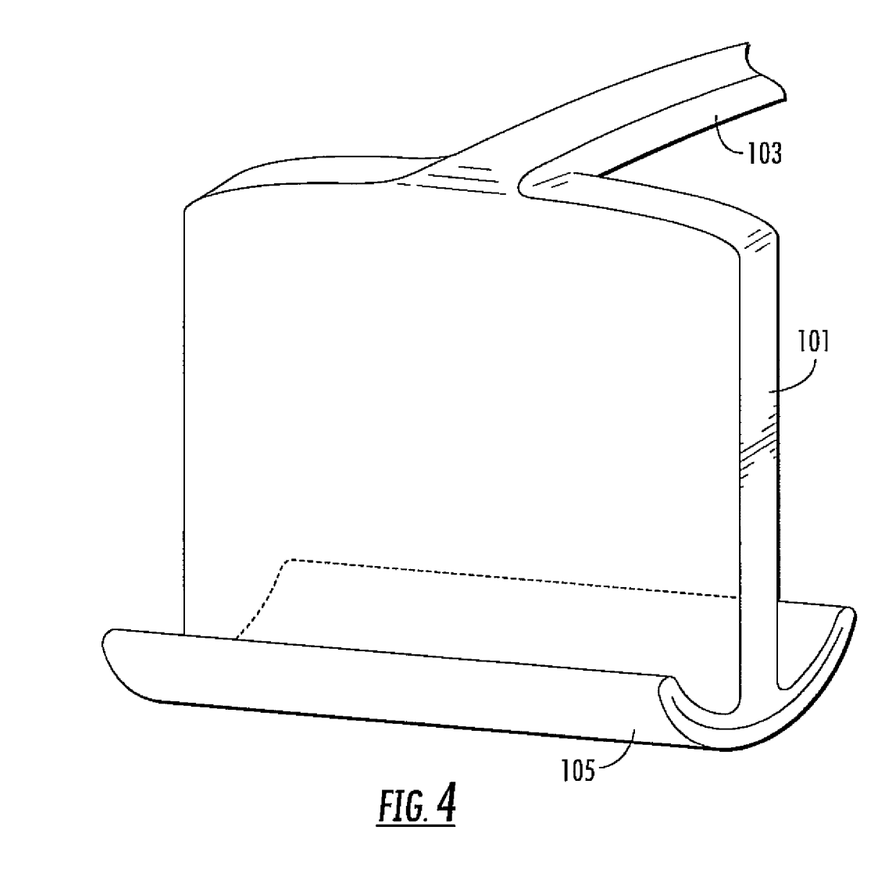
FIG. 4 is an exemplary partial side perspective view of a retractor in a compressed position according to an aspect of the present invention.
Figure 5:
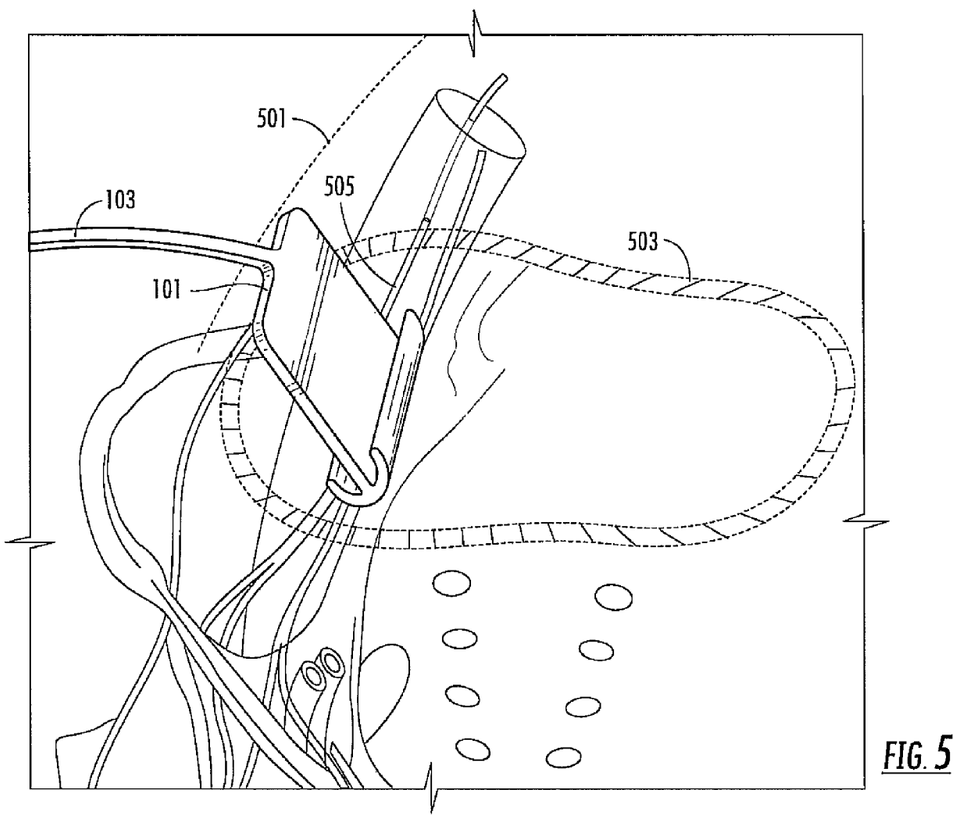
FIG. 5 is an exemplary view of a retractor assembly positioned during insertion and placement within an abdominal incision according to an aspect of the present invention.

According to one aspect of the present invention, the elongate member 105 comprised of an extremely pliable, flexible material having a hexagonal cross-section or 'honeycomb' shape provides a configuration specially adapted to self-molding to the shape of the retro-peritoneal space in the human abdominal cavity, as discussed further with respect to FIGS. 3-5.

The wall 202 may further comprise an internal cell lattice structure 203, for example, an air-filled network of cells. For example, as shown in part A of FIG. 2B, the wall 202 may include an internal 'cross-linked' cell network 203 in a 'honeycomb' configuration.

The cavity 107 may comprise a hollow open air chamber or may also include an internal cell lattice structure 201, e.g., a collection of flexible air-filled cross-linked cells having a multi-sided configuration. For example, as shown e.g., in FIG. 2A the cavity 107 may include an internal lattice network of cells 201 in a 'honeycomb' configuration wherein a longitudinal axis of the air chambers is substantially parallel to a longitudinal axis 106 of the elongate member 105.

Preferably in both the cell network of the cavity 201 and/or the cell network of the walls 203, an open-cell configuration is employed, such that the air within the cells may escape when the cells are compressed. For example, the elongate member 105 may be open-ended so as to allow air to escape from each end during compression. Accordingly, the elongate member 105 is adapted to be freely and easily compressible and moldable to the shape of any surface it is contacted with, with minimal resiliency.

The cell network of the cavity 201 and/or the cell network of the walls 203 are also preferably comprised of a thin, flexible, soft, medical-grade material safe for use within the human body, e.g., polyurethane.

It is noted that according to one embodiment, the deformable elongate member 105 may be configured to be attached to frames of existing surgical retractors, e.g., attached onto a desired/suitable edge of any other existing retractor frame for use therewith. In other words, existing retractors may be easily retrofitted with the elongate member 105. Thus advantageously, the beneficial properties of the elongate member 105 may be imparted onto existing surgical retractors, such as rigid metal frame retractors.

FIGS. 3 and 4 are exemplary side and partial perspective views, respectively, of a retractor in a compressed position, erg., during use, according to an aspect of the present invention.

According to one exemplary aspect of the present invention, the elongate member 105 is comprised of an extremely pliable, flexible material having a substantially hexagonal cross section or 'honeycomb' shape that is specially adapted to form a U-shape when compressed within the retro-peritoneal space in the human abdominal cavity, thus self-molding to U-shape of the retroperitoneal space and providing shock absorption and cushioning to the tissues, blood vessels, nerves, etc., upon which it is pressed against. The exemplary U-shape assumed by the elongate member 105 during such self-molding is depicted in FIG. 3. Preferably, the ends 303 of the U-shape have blunted or rounded edges 303 for improved safety.

An exemplary thickness 301 of the blade 101 may comprise e.g., about ⅛ inch to about ¼ inch. Alternate thicknesses may be contemplated.

The retractor 100 may further include devices such as sensory perception and pressure sensors (not shown), to provide real-time feedback to the surgeon regarding, e.g., pressure readings within or at the incision site. Such feedback devices may be oriented on the retractor 100 at any location at which such data is desired to be captured and analyzed.

FIG. 5 is an exemplary view of a retractor assembly positioned upon insertion and placement within an abdominal incision 503. For example, the retractor 100 is preferably placed so as to lie lengthwise along the retroperitoneal space 505. Once the retractor 100 is positioned accordingly with the desired amount of downwards force, the elongate member 105 spreads and conforms to fit the shape of the pelvic/abdominal sidewall 501 and retroperitoneal space 505, in this instance assuming a U-shape.

It is noted that by virtue of its flexible properties, configuration and responsiveness to pressure, the elongate member 105 may assume varying degrees of a generalized U-shape, in proportion and in response to the amount of force which is being applied to it. Accordingly, an advantageous shock absorbing effect as well as a customizable fit or "self-molding" feature is provided.

Another important benefit is the adaptive ability of the elongate member 105 to provide and optimize a uniform distribution of force over a greater surface area, e.g., by custom molding to the shape of the surface with which it is contacted. By distributing the force over a greater surface area, pressure points which might have been caused by the blade-shaped unit 101 are reduced or eliminated when the force is applied or exerted. Accordingly, damage or injury to the underlying sensitive tissue areas subject to the force is prevented.

Figure 6:
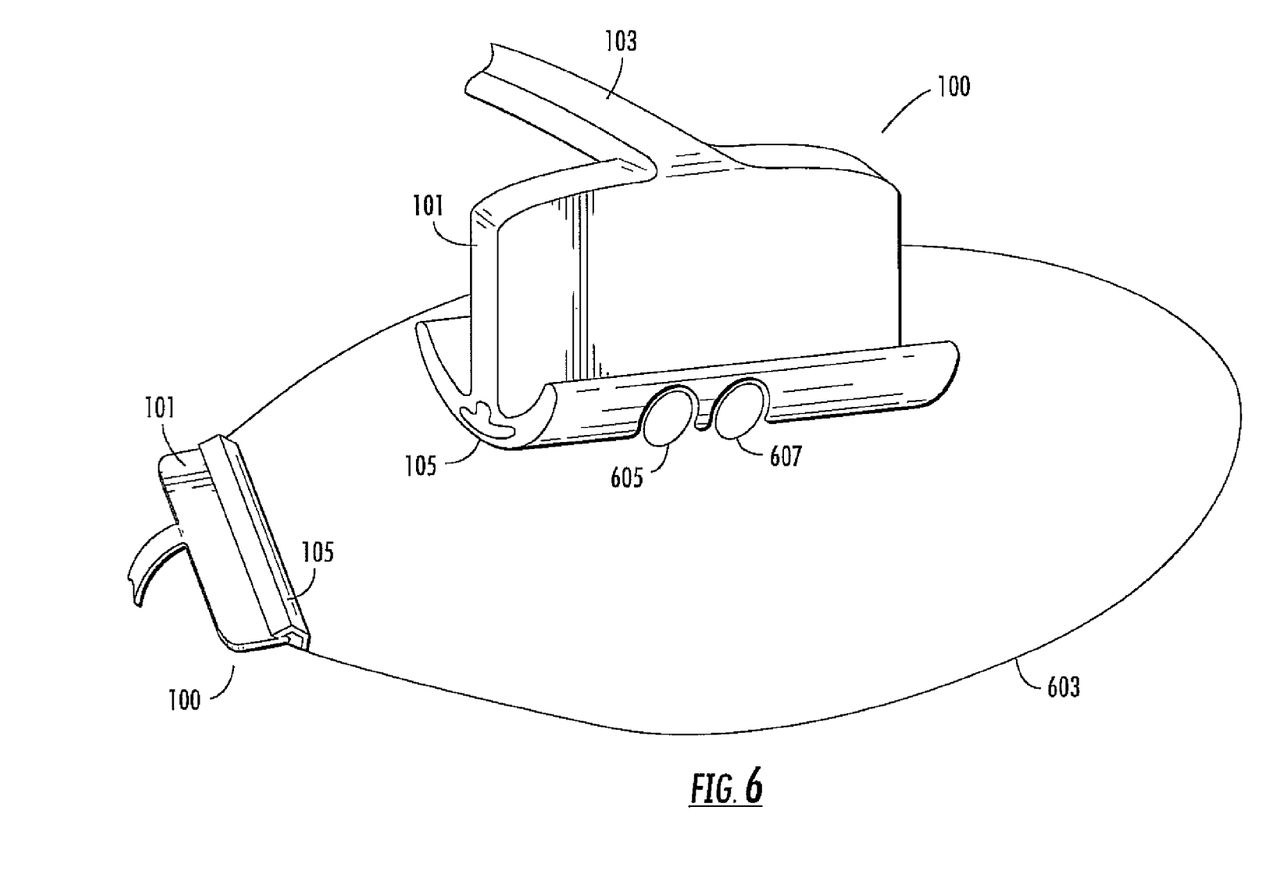
FIG. 6 is an exemplary depiction of a plurality of retractor assemblies positioned within an abdominal incision, for example at a top and side location thereof, according to an aspect of the present invention.

FIG. 6 is an exemplary depiction of a plurality of retractor assemblies 100 positioned within an abdominal incision 603, for example at a top and side location thereof, according to an aspect of the present invention. Advantageously, a retractor 100 may be positioned at various locations, e.g., upper, lower and/or lateral regions of an incision to maintain a desired opening size and/or shape. Namely, the retractor 100 may be safely used at various regions of an incision such as within the upper and lower abdomen due to the configuration and characteristics of the pliable, soft elongate member 105 which naturally conforms to and retracts, e.g., the large and small bowels without restricting the blood flow of the aorta 605 and/or vena cava 607.

A retractor according to the present invention enables uniform distribution of pressure and is readily deformable over the large vessels, which helps prevent the blockage of blood flow to the lower pelvis and abdomen and bladder injuries. This provides the patient with better blood return (Frank Startlings Law) which ensures higher patient stability and a more normal blood pressure Thus, injuries such as bowel ileus and aortic/vena cava vascular injuries (which could lead to pulmonary embolism) are prevented. In addition, the time consuming step of packing the upper abdomen and side walls with sponges (which is not only time consuming but risks the possible loss of packs left inside the patient), is eliminated.

Further, the retractor may be used in a lower region of the abdomen, which will help decrease post-operative urinary retention and enable better urine output during surgery due to the more uniform bladder and ureter retraction and resultant reduced trauma and injury to the bladder nerves.

Using a retractor according to the present invention with its curved handle having flexion and a deformable, soft elongate member eliminates the need for surgeons to pack the pelvis and the upper abdomen with sponges in attempts to prevent injury to the upper and lower abdomen.

Finally, the flexion and downward curve of the handle gives the surgeons more room to physically move themselves closer to the patient and offers them improved visual exposure. Thus, the surgeons have a better mechanical advantage due to their improved range of motion, which also prevents fatigue.

Although the embodiment which incorporates the teachings of the present invention has been shown and described in detail herein, those skilled in the art can readily devise many other varied embodiments that still incorporate these teachings. Having described preferred embodiments for a flexible surgical retractor (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, what is claimed and desired protected by Letters Patent is set forth in the appended claims.

What is claimed is:

1. A surgical retractor comprising:
   a unit having a first edge and a second opposing edge; and
   a deformable, resilient elongate member defining an open-ended cavity in a first configuration, wherein an exterior surface of the elongate member is attached to the first edge of the unit and the elongate member is comprised of a cell lattice structure and is configured to be compressible and moldable to a surface, whereby the elongate member is configured to absorb shock in at least a direction substantially parallel to a vertical axis connecting the first edge to the second opposing edge, wherein the elongate member is moldable into a second configuration wherein the elongate member is compressed to substantially eliminate the cavity, and wherein each cell of the cell lattice structure has side walls defining a chamber and wherein a longitudinal axis of each chamber of each cell is substantially parallel to a longitudinal axis of the elongate member.

2. The retractor of claim 1, wherein the elongate member is at least one of a polygonal or circular shape in cross-section.

3. The retractor of claim 1, further comprising a curved handle attached to the second edge.

4. The retractor of claim 1, wherein the surface comprises a human tissue surface within the human abdominal cavity.

5. The retractor of claim 4, wherein the surface comprises a retroperitoneal space.

6. The retractor of claim 1, wherein in the second configuration the elongate member is moldable into a U-shape.

7. The retractor of claim 1, wherein the elongate member is comprised of flexible polyurethane.

8. The surgical retractor of claim 1, wherein the exterior surface of the elongate member includes a longitudinal edge, whereby the elongate member is affixed to said first edge of the unit along said longitudinal edge.

9. A self-molding surgical retractor comprising:
   a unit having a first edge and a second opposing edge;
   a deformable, resilient elongate member defining an open-ended cavity in a first configuration, wherein an exterior surface of the elongate member is attached to the first edge of the unit and the elongate member is comprised of a cell lattice structure and is configured to be compressible and moldable to a surface, whereby the elongate member is configured to absorb shock in at least a direction substantially parallel to a vertical axis connecting the first edge to the second opposing edge; and
   a curved handle attached to the second edge, wherein the elongate member includes an internal flexible cell lattice structure and is moldable into a second configuration wherein the elongate member is compressed to substantially eliminate the cavity, and wherein each cell of the cell lattice structure has side walls defining a chamber, wherein a longitudinal axis of each chamber of each cell is substantially parallel to a longitudinal axis of the elongate member.

10. The retractor of claim 9, wherein a cross-section of the elongate member comprises at least one of a polygonal or circular shape.

11. The retractor of claim 9, wherein the cell lattice structure comprises a plurality of hexagonal flexible cells.

12. The retractor of claim 9, wherein the surface comprises a human tissue surface within the human abdominal cavity.

13. The retractor of claim 9, wherein the elongate member is comprised of flexible polyurethane.

14. A surgical retractor comprising:
   a deformable polyurethane elongate member comprising an open-ended elongate enclosure defining an open-ended chamber, wherein the elongate member is comprised of a cross-linked cell network in a honeycomb configuration and is configured to be compressible, resilient and moldable with respect to a surface, wherein the elongate member includes an internal flexible cell lattice structure, said elongate member being moldable into a configuration wherein the elongate member is compressed to substantially eliminate the cavity, and wherein each cell of the cell lattice structure has side walls defining a chamber, wherein a longitudinal axis of each chamber of each cell is substantially parallel to a longitudinal axis of the elongate member.

* * * * *